United States Patent
Begg et al.

(10) Patent No.: US 11,744,605 B2
(45) Date of Patent: Sep. 5, 2023

(54) TISSUE RESECTING DEVICE WITH DEFLECTABLE TIP

(71) Applicant: Covidien LP, Mansfield, MA (US)

(72) Inventors: Nikolai D. Begg, Wellesley, MA (US); Lisa M. Quealy, Woburn, MA (US)

(73) Assignee: Covidien LP, Mansfield, MA (US)

( * ) Notice: Subject to any disclaimer, the term of this patent is extended or adjusted under 35 U.S.C. 154(b) by 678 days.

(21) Appl. No.: 16/836,057

(22) Filed: Mar. 31, 2020

(65) Prior Publication Data
US 2021/0298782 A1    Sep. 30, 2021

(51) Int. Cl.
*A61B 17/32*    (2006.01)
*A61B 17/00*    (2006.01)

(52) U.S. Cl.
CPC .. *A61B 17/32002* (2013.01); *A61B 17/00234* (2013.01); *A61B 2017/00238* (2013.01); *A61B 2017/320028* (2013.01); *A61B 2017/320032* (2013.01)

(58) Field of Classification Search
CPC ........ A61B 17/32002; A61B 17/00234; A61B 17/320758; A61B 17/320725; A61B 17/32075; A61B 17/42; A61B 17/320783; A61B 2017/00238; A61B 2017/320028; A61B 2017/320032; A61B 2017/320791; A61B 2017/320775; A61B 2017/320766; A61B 2017/4216; A61B 2017/00309;

(Continued)

(56) References Cited

U.S. PATENT DOCUMENTS

| 5,085,658 A | 2/1992 | Meyer |
| 5,152,744 A | 10/1992 | Krause |
| 5,529,580 A | 6/1996 | Kusunoki et al. |

(Continued)

FOREIGN PATENT DOCUMENTS

| DE | 20 2009 012796 U1 | 11/2009 |
| WO | 2019038773 A1 | 2/2019 |

OTHER PUBLICATIONS

Extended European Search Report issued in corresponding European Application No. 21166204.4 dated Jul. 30, 2021, 7 pages.

(Continued)

*Primary Examiner* — Erich G Herbermann
(74) *Attorney, Agent, or Firm* — Carter, DeLuca & Farrell LLP

(57) ABSTRACT

A tissue resecting device includes a housing having an outer shaft extending therefrom, the outer shaft including a tool portion disposed at a distal end thereof, the tool portion having a window defined therein. A rotatable inner shaft is disposed within the outer shaft and includes a cutting member disposed at the distal end thereof in concentric alignment with the tool portion and configured to rotate concomitantly with the inner shaft. The cutting member includes a series of slots defined therein configured to facilitate articulation of the cutting member and a blade disposed at a distal end thereof configured to cut tissue upon rotational engagement therewith. An actuator is configured to articulate the tool portion and the cutting member upon actuation thereof between a neutral position wherein the blade is aligned for radial cutting and articulated positions wherein the blade is aligned for varying degrees of axially-aligned cutting.

16 Claims, 4 Drawing Sheets

(58) Field of Classification Search
CPC ............ A61B 18/1445; A61B 18/1485; A61B 2018/00601; A61B 2018/1412
See application file for complete search history.

(56) References Cited

U.S. PATENT DOCUMENTS

| | | | |
|---|---|---|---|
| 5,690,660 A * | 11/1997 | Kauker | A61B 17/32002 |
| | | | 604/902 |
| 5,766,199 A | 6/1998 | Heisler et al. | |
| RE38,018 E | 3/2003 | Anctil et al. | |
| 7,699,846 B2 * | 4/2010 | Ryan | A61B 17/32002 |
| | | | 606/177 |
| 8,528,563 B2 | 9/2013 | Gruber | |
| 2008/0097470 A1 | 4/2008 | Gruber et al. | |
| 2008/0245371 A1 | 10/2008 | Gruber | |
| 2014/0012255 A1 | 1/2014 | Smith et al. | |
| 2015/0066033 A1 * | 3/2015 | Jorgensen | A61B 34/71 |
| | | | 606/170 |
| 2019/0183528 A1 | 6/2019 | Sullivan et al. | |

OTHER PUBLICATIONS

Extended European Search Report issued in corresponding European Application No. 21166204.4 dated Jan. 31, 2023, 5 pages.

* cited by examiner

TISSUE RESECTING DEVICE WITH DEFLECTABLE TIP

BACKGROUND

1. Technical Field

The present disclosure relates generally to the field of tissue resection. In particular, the present disclosure relates to a tissue resecting device including a selectably deflectable cutting member.

2. Background of Related Art

Tissue resection may be performed endoscopically within an organ, such as a uterus, by inserting an endoscope (or hysteroscope) into the uterus and passing a tissue resection device through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

As used herein, the term "distal" refers to the portion that is described which is farther from a user, while the term "proximal" refers to the portion that is described which is closer to a user. Further, to the extent consistent, any or all of the aspects described herein may be used in conjunction with any or all of the other aspects described herein.

In accordance with an aspect of the present disclosure, a tissue resecting device includes a housing having an elongated outer shaft extending from a distal end thereof, the outer shaft including a tool portion disposed at a distal end thereof, the tool portion including a window defined therein. An inner shaft is disposed within the elongated outer shaft and includes proximal and distal ends. The inner shaft is configured to rotate upon actuation thereof and includes a cutting member disposed at the distal end thereof in concentric alignment with the tool portion. The inner shaft is configured to rotate concomitantly with the inner shaft. The cutting member includes a series of slots defined therein configured to facilitate articulation of the cutting member and a blade disposed at a distal end thereof configured to cut tissue upon rotational engagement therewith, the blade operably disposed within the window of the tool portion. An actuator is operably disposed on the housing and is configured to articulate the tool portion and the cutting member upon actuation thereof between a neutral position wherein the blade is aligned for radial cutting and one or more articulated positions wherein the blade is aligned for varying degrees of axially-aligned cutting.

In aspects according to the present disclosure, the tool portion is made from an articulatable material, e.g., a super elastic alloy. In other aspects according to the present disclosure, the blade is spaced from a distal end of the window of the tool portion allowing the blade to cut tissue in a more axially-aligned fashion when the tool portion and cutting member are articulated to the articulated position. In yet other aspects according to the present disclosure, the tool member and the cutting member are articulatable in a range of about 0 degree and about 90 degrees.

In aspects according to the present disclosure, the elongated outer shaft further includes an articulation cable coupled to a distal portion of the tool portion, such that axial displacement of the cable causes articulation of the tool portion and the cutting member between the neutral position and articulated positions. In aspects according to the present disclosure, the elongated outer shaft further includes one or more guide members configured to receive and guide the articulation cable therethrough.

In aspects according to the present disclosure, the tissue resecting device also includes outflow tubing adapted to connect to a fluid management system configured to provide negative pressure to the outer shaft to aspirate fluids through the window and draw tissue into engagement with the blade. In other aspects according to the present disclosure, a motor is disposed within the housing and is configured to operably couple to the inner shaft and provide rotation thereto upon activation thereof.

In accordance with another aspect of the present disclosure, a tissue resecting device includes a housing having an elongated outer shaft including a tool portion disposed at a distal end thereof, the tool portion including a cuff at a distal end thereof and a window defined therein. An inner shaft is disposed within the elongated outer shaft and includes proximal and distal ends. The inner shaft is configured to rotate upon actuation thereof and includes a cutting member disposed at the distal end thereof in concentric alignment with the tool portion and configured to rotate concomitantly with the inner shaft. The cutting member includes a series of slots defined therein configured to facilitate articulation of the cutting member and cut tissue upon rotational engagement therewith and a blade disposed at a distal end thereof configured to cut tissue upon rotational engagement therewith. The blade is selectively translatable between a neutral position wherein the blade is housed within the distal cuff of the tool member and a cutting position wherein the blade is aligned with the window of the tool portion. An actuator is operably disposed on the housing and is configured to articulate the tool portion and the cutting member upon actuation thereof between a neutral position wherein the series of slots is aligned for radial cutting and one or more articulated positions wherein the blade, when translated to the cutting position, is aligned for varying degrees of axially-aligned cutting.

In aspects according to the present disclosure, the tool portion is made from an articulatable material, e.g., a superelastic alloy. In other aspects according to the present disclosure, the tool member and the cutting member are articulatable in a range of about 0 degree and about 90 degrees.

In aspects according to the present disclosure, the elongated outer shaft further includes an articulation cable coupled to a distal portion of the tool portion, such that axial displacement of the cable causes articulation of the tool portion and the cutting member between the neutral position and articulated positions. In yet other aspects according to the present disclosure, the elongated outer shaft further includes one or more guide members configured to receive and guide the articulation cable therethrough.

In aspects according to the present disclosure, the tissue resecting device further includes outflow tubing adapted to connect to a fluid management system configured to provide negative pressure to the outer shaft to aspirate fluids through the window and draw tissue into engagement with the series of slots or the blade. In yet other aspects according to the present disclosure, the tissue resecting device further includes a motor disposed within the housing and configured to operably couple to the inner shaft and provide rotation thereto upon activation thereof.

In aspects according to the present disclosure, the series of slots is laser cut, die-stamped or coined.

BRIEF DESCRIPTION OF THE DRAWINGS

Various aspects and features of the present disclosure are described hereinbelow with reference to the drawings wherein like numerals designate identical or corresponding elements in each of the several views and.

DETAILED DESCRIPTION

Figure 1:
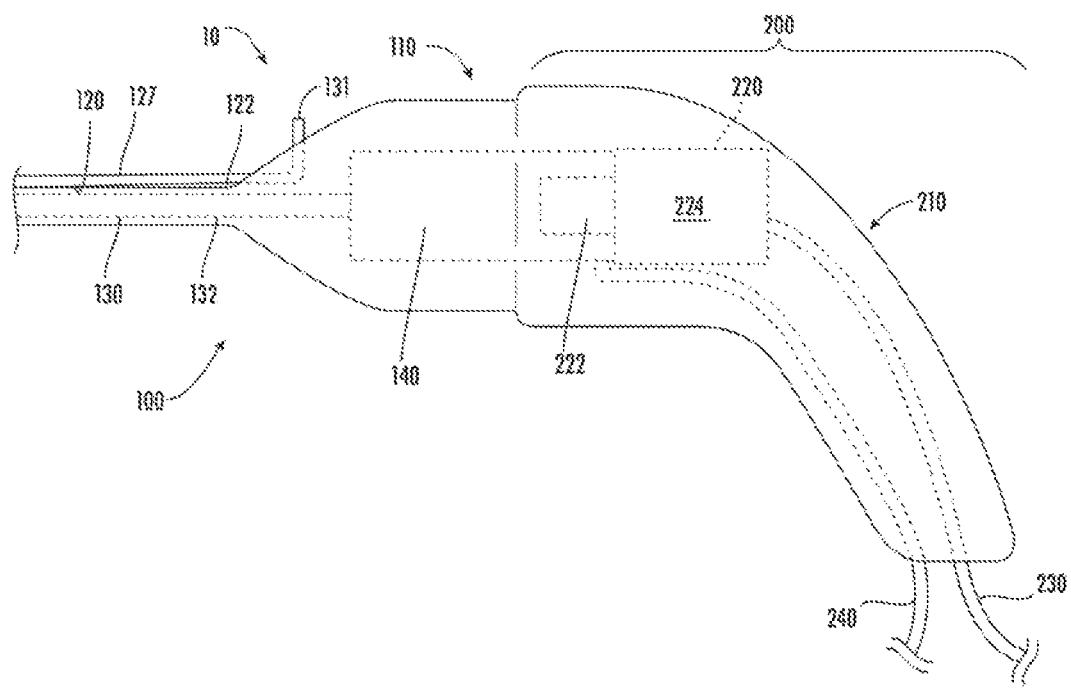
FIG. 1 is a partial side view of a proximal portion of a tissue resecting device in accordance with an aspect of the present disclosure.

Referring generally to FIG. 1, a tissue resecting device 10 provided in accordance with the present disclosure and configured to resect tissue includes an end effector assembly 100 and a handpiece assembly 200. Tissue resecting device 10 is adapted to connect to a control unit (not shown), e.g., via cable 230, to provide power and control functionality to tissue resecting device 10, although tissue resecting device 10 may alternatively or additionally include controls associated with handpiece assembly 200 and/or a power source, e.g., battery, disposed within handpiece assembly 200. In other embodiments, tissue resecting device 10 is manually powered and/or controlled. Tissue resecting device 10 is further adapted to connect to a fluid management system (not shown), e.g., via outflow tubing 240, for removing fluid, tissue, and debris from a surgical site via tissue resecting device 10. The control unit and fluid management system may be integral with one another, coupled to one another, or separate from one another.

With continued reference to FIG. 1, tissue resecting device 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, handpiece assembly 200 may be configured as a cleanable/sterilizable, reusable component, while end effector assembly 100 is configured as a single-use, disposable/reprocessable component. In either of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for use of different end effector assemblies with handpiece assembly 200.

Figure 4:
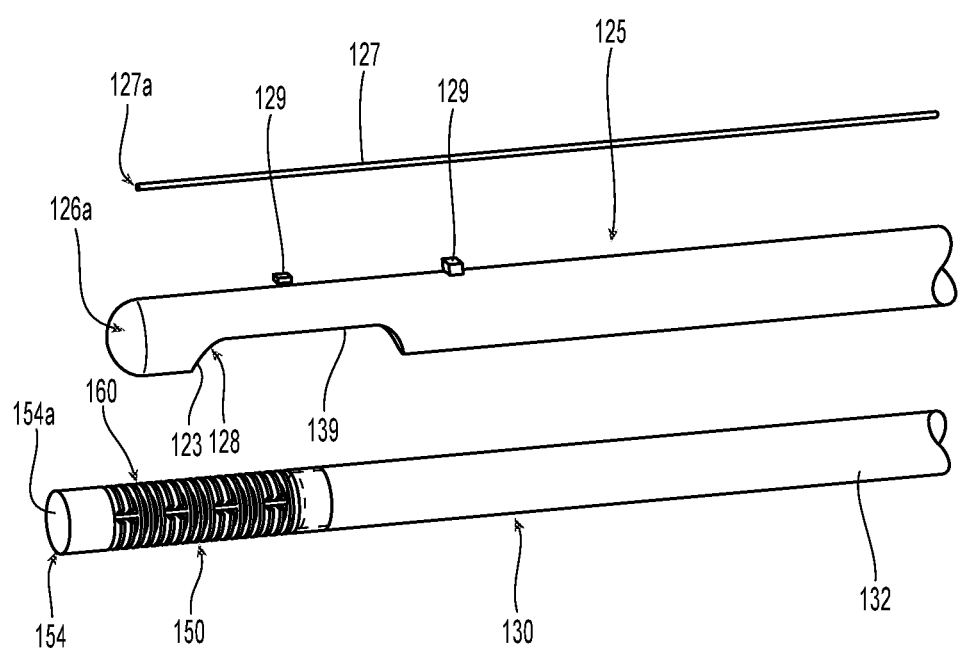
FIG. 4 is an exploded perspective view of the distal portion of the end effector assembly of FIG. 2, with parts separated.

End effector assembly 100 includes a proximal hub housing 110, an elongated outer shaft 120 fixedly engaged with and extending distally from proximal hub housing 110, an inner cutting shaft 130 movably disposed within elongated outer shaft 120, an inner drive core 140, and a cutting member 150 (FIG. 4). Inner drive core 140 is operably disposed within proximal hub housing 110 and coupled to inner cutting shaft 130 such that rotational input imparted to inner drive core 140, e.g., via handpiece assembly 200, drives rotation of inner cutting shaft 130 within and relative to elongated outer shaft 120. In embodiments, inner cutting shaft 130 may be configured to additionally or alternatively reciprocate relative to elongated outer shaft 120.

Proximal hub housing 110 of end effector assembly 100 is configured to releasably engage handle housing 210 of handpiece assembly 200, e.g., via snap-fit, threaded, luer-lock, lock-button, or other suitable engagement, and may be configured for fixed engagement with handle housing 210 or rotational engagement therewith.

Figure 2:
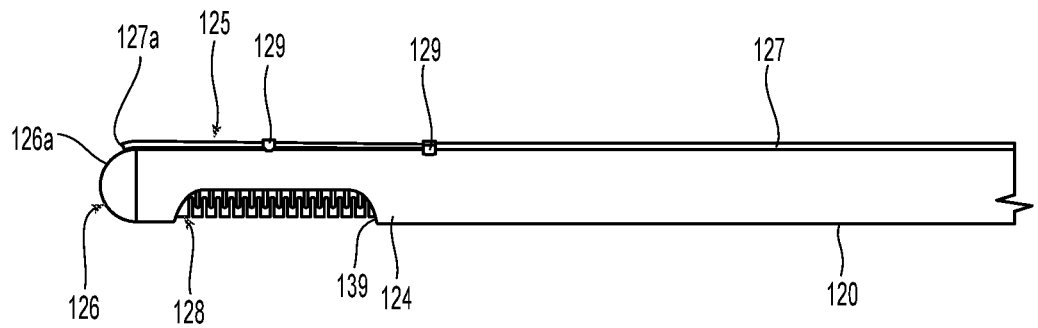
FIG. 2 is a partial side view of a distal portion of an end effector assembly of the tissue resecting device of FIG. 1.

With reference now to FIGS. 1 and 2, elongated outer shaft 120 of end effector assembly 100 includes a proximal end portion 122 extending into and fixedly engaged within proximal hub housing 110, and a distal end portion 124 including a tool portion 125. Elongated outer shaft 120 may be formed as a single construct. For example, elongated outer shaft 120 may be monolithically formed. Tool portion 125 includes a closed distal end 126 having a tip 126a and defines a window 128 proximally-spaced from closed distal end 126.

Figure 3:
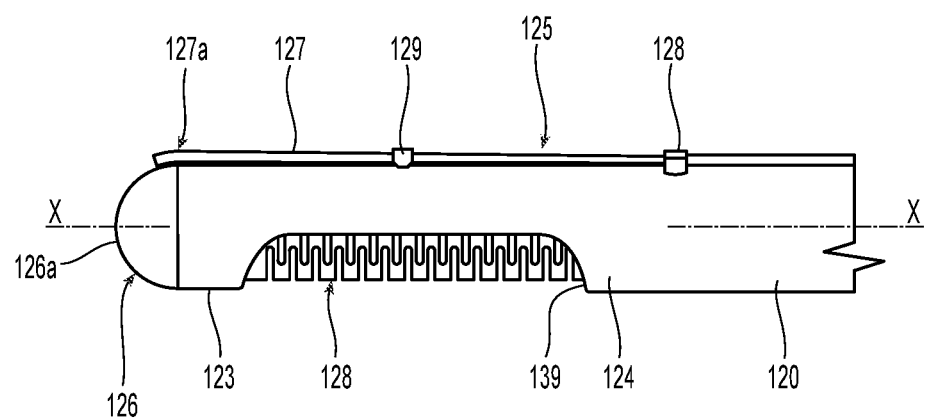
FIG. 3 is a partially enlarged side view of a distal end portion of the end effector assembly of FIG. 2, disposed in a neutral position.
Figure 5:
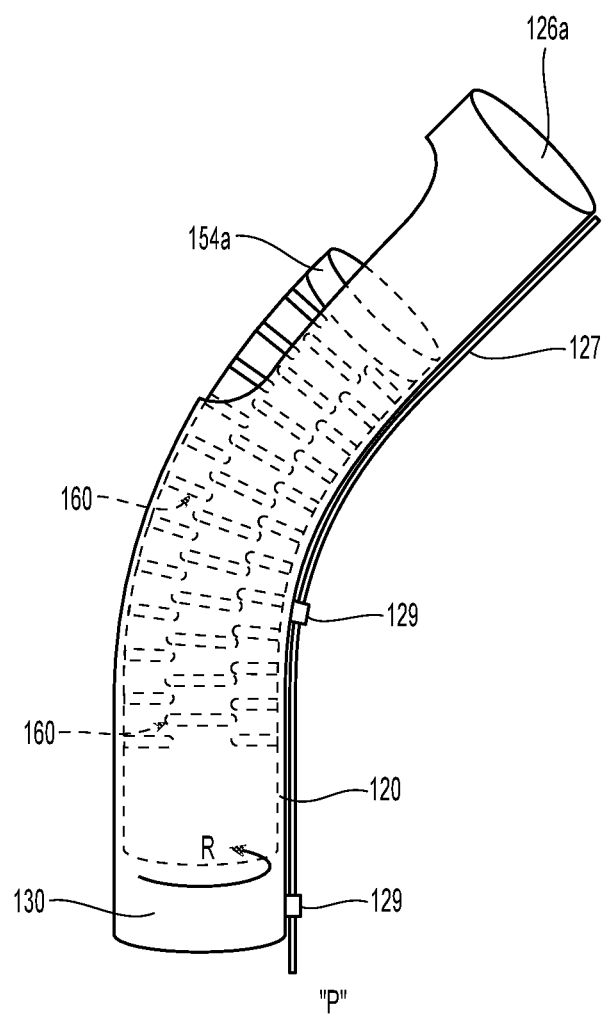
FIG. 5 is a partially enlarged side view of the distal end portion of the end effector assembly of FIG. 2, disposed in an articulated position.

With reference to FIGS. 3 and 4, tool portion 125 of elongated outer shaft 120 is made from a superelastic, deformable or articulatable material to allow selective articulation of the tool member 125. More particularly, in order to effect articulation of tool portion 125, tool portion 125 is operably coupled to an articulation cable 127. A distal end 127a of articulation cable 127 is fixedly coupled to tip 126a (FIG. 1) of elongated outer shaft 120 and a proximal portion is coupled to an actuator 131 to allow selective articulation thereof. Tool portion 125 further includes one or more guide members 129 configured to receive articulation cable 127 therethrough to facilitate axial displacement of articulation cable 127. Under such a configuration, axial displacement of articulation cable 127 (See FIG. 5, direction "P") effects articulation of tool portion 125 (and cutting member 150 as explained below) between a neutral position (FIG. 3) and an articulated position (FIG. 5). Actuator, e.g., a lever or a knob 131 (FIG. 1), may be provided on proximal hub housing 110 of end effector assembly 100 (as shown) or on handpiece assembly 200 (FIG. 1) to effect axial displacement of articulation cable 127.

With reference to FIG. 4, inner cutting shaft 130 includes a proximal end portion 132 (FIG. 1) and a distal end portion 134 coupled to cutting member 150 for concomitant rotation therewith. Cutting member 150 may be detachably coupled to distal end portion 134, e.g., via snap-fit, threaded, luer-lock, lock-button, or other suitable engagement, and may be configured for fixed engagement with inner cutting shaft 130. However, it is also contemplated that cutting member 150 may be monolithically formed with or otherwise permanently connected to inner cutting shaft 130.

Cutting member 150 includes a series of slots 160 defined therein and extending distally from a proximal end thereof and a closed distal end 154. Slots 160 are disposed along a length of the cutting member 150 and are configured to enable the cutting member 150 to selectively articulate with articulation of tool portion 125. Axial displacement of articulation cable 127 in the direction "P" effects articulation of tool portion 125 and the cutting member 150 between a neutral position (FIG. 3) and an articulated position (FIG. 5).

A distal end 154 of the cutting member 150 is spaced relative to the distal end 126 of the tool portion 125 exposing a blade 154a within window 128. When disposed in the neutral position, the blade 154a is configured to rotate and radially cut tissue that is drawn into window 128. A surgeon translates or rotates the tool portion 125 relative to the tissue allowing the blade 154a to radially cut tissue.

To access more difficult tissue, the surgeon can articulate the tool portion 125 and cutting member 150 via proximal actuation of cable 127 which articulates the tool portion 15 (and cutting member 150) within a range of about zero degrees (0°—the neutral position) to about ninety degrees (90°). As the blade 154a articulates, the blade 154a becomes more axially aligned allowing the surgeon to access more distally-oriented tissue. The surgeon can easily switch back and forth between various blade 154a cutting positions (from fully radially-aligned to fully distally aligned or any angle therebetween).

In alternative embodiments, the slots 160 may include sharpened inner peripheral surfaces to allow the slots 160 to radially cut tissue when drawn into window 128 during rotation of the cutting member 150. More particularly, these "cutting" slots 160 are aligned on cutting member 150 such that cutting slots 160 engage and cut tissue in a radially aligned manner (from a side thereof) as the tissue is drawn against window 128. In this instance, cutting member 150 may be translated and rotated to cut tissue in engagement with cutting slots 160. Cutting slots 160 may be stamped or laser cut to produce a nice sharp edge for engaging and cutting tissue. Other features may be included with the cutting slots 160 to enhance tissue engagement and eventual cutting during rotation and/or translation, e.g., beveled edges, gripping features, serrations, etc.

As mentioned above, blade 154a is configured to cut tissue when the cutting member 150 rotated and/or translated. In other embodiments, to expose the blade 154a for cutting, cutting member 150 may be translated to space the blade 154a from the distal end 126 of the tool portion 125 of the outer shaft 120 to expose the blade 154a in window 128. The distal end 126 of shaft 128 may then be articulated via proximal translation of cable 127 (FIG. 5) which, in turn, partially frees the blade 154a from the window 128 (or at the very least re-orients the blade 154a) and allows the blade 154a to engage tissue in a more axially-aligned manner. The blade 154a may be translated or rotated to cut tissue in this fashion.

In this alternate embodiment, the cutting slots 160 of cutting member 150 allow the cutting member 150 to selectively articulate along with the tool portion 125 of the outer shaft 120. When the cutting member 150 is at a distal-most position, the blade 154a is trapped within a distal cuff 123 forcing the cutting member 150 to articulate with the tool portion 125. When the cutting member 150 is translated proximally, the blade 154a disengages from distal cuff 123 and deflects relative to window 128 to allow the blade 154a to cut tissue in a more distally-oriented fashion. As such, the cutting member 150 with the cutting slots 160 may cut tissue in a radially-oriented manner by rotating the cutting member 150 relative to the tool portion 125 and, if needed, the surgeon can expose the distal blade 154a to cut more distally-oriented tissue (via translation or rotation of blade 154a) depending on the position and design of the blade 154a.

With continued reference to FIGS. 1, 4 and 5, inner cutting shaft 130 is rotatable relative to elongated outer shaft 120. Inner cutting shaft 130 may be continuously rotated in a single direction or may be configured to reverse and move in opposite directions. In either configuration, rotation of inner cutting shaft 130 relative to elongated outer shaft 120 defines one or more positions of end effector assembly 100, wherein inner cutting shaft 130 is oriented relative to elongated outer shaft 120 such that cutting slots 160 of cutting member 150 at least partially overlap window 128 of tool portion 125 of elongated outer shaft 120, thus enabling fluid communication therebetween.

In embodiments, window 128 not only provides access to the interior of elongated outer shaft 120 to engage the blade 154a or cutting slots 160 as described above, but may be surrounded by a cutting edge 139 about the inner peripheral surface of the window 128 so as to facilitate cutting of tissue passing through window 128 and into elongated outer shaft 120. Alternatively, window 128 may define geometry to facilitate introduction of tissue into engagement with the cutting slots 160 or blade 154a, e.g., beveled edging, serrations, coated surfaces, etc.

Referring back to FIG. 1, handpiece assembly 200 generally includes a handle housing 210, a drive assembly 220 disposed within handle housing 210, a cable 230, and an outflow tubing 240. Handle housing 210 is configured to releasably engage proximal hub housing 110 of end effector assembly 100, and defines a pistol-grip configuration, although other configurations are also contemplated, e.g., a pencil-grip configuration. Handpiece assembly 200 may further include one or more controls (not shown) disposed on or operably associated with handle housing 210 to facilitate activation of drive assembly 220 or displacement of articulation cable 127 in a desired manner. For example, handpiece assembly 200, rather than proximal hub housing 110 of end effector assembly 100 (as shown), may include the dial or lever 131 that is operatively coupled to articulation cable 127 to axially displace articulation cable 127.

Drive assembly 220 includes a distal drive rotor 222 and a motor 224 that drives rotation of distal drive rotor 222. Distal drive rotor 222 is configured to mate with inner drive core 140 of end effector assembly 100 upon engagement of end effector assembly 100 with handpiece assembly 200 to thereby engage distal drive rotor 222 and inner drive core 140 with one another. Cable 230 provides power and/or control signals to motor 224 to control rotation of distal drive rotor 222.

Outflow tubing 240 is configured such that, with end effector assembly 100 engaged with handle housing 210, outflow tubing 240 communicates with the internal lumen of inner cutting shaft 130 of end effector assembly 100 to receive resected tissue as well as fluid and other debris withdrawn from an internal surgical site during use. Outflow tubing 240 is configured to ultimately connect to a collection canister (not shown) or other suitable collection reservoir for collecting the tissue, fluid, and debris withdrawn from the internal surgical site. Outflow tubing 240 may additionally or alternatively couple to a suction source (not shown) for establishing suction or negative pressure through outflow tubing 240 and the with the internal lumen of inner cutting shaft 130 to facilitate drawing tissue, fluid, and debris into and through inner cutting shaft 130.

Inner drive core 140 extends proximally from proximal hub housing 110 of end effector assembly 100 and is configured to engage distal drive rotor 222 of a drive assembly 220. At least a portion of distal drive rotor 222 defines a non-circular cross-section that is complementary to that of the lumen of inner drive core 140 such that engagement of distal drive rotor 222 with inner drive core 140 rotationally fixes distal drive rotor 222 with inner drive core 140. In addition, inner drive core 140 extends distally through proximal hub housing 110 and is (directly or indirectly) fixedly engaged with proximal end portion 132 of inner cutting shaft 130 within proximal hub housing 110.

Under such a configuration, rotation of inner drive core 140 imparts rotation to inner cutting shaft 130. Thus, with end effector assembly 100 engaged with handpiece assembly 200, motor 224 may be activated to drive rotation of distal drive rotor 222, thereby driving rotation of inner cutting shaft 130 relative to elongated outer shaft 120.

In order to engage end effector assembly 100 with handpiece assembly 200, end effector assembly 100, led by inner drive core 140, is inserted into handle housing 210 of handpiece assembly 200. Upon further insertion of end effector assembly 100 into handpiece assembly 200, inner drive core 140 is slid about distal drive rotor 222 to thereby rotatably engage distal drive rotor 222 and inner drive core 140 with one another.

Once tissue resecting device 10 is assembled, e.g., once end effector assembly 100 is engaged with handpiece assembly 200 as detailed above, tissue resecting device 10 is ready for use. In use, tissue resecting device 10 is positioned within an internal body cavity or organ, e.g., a uterus, such that the distal end portion of end effector assembly 100 is positioned adjacent tissue to be removed. Articulation cable 127 may be displaced to articulate the distal end portion of end effector assembly 100 to better position the distal end portion of end effector assembly 100 adjacent tissue to be removed. Tissue resecting device 10 may be inserted through an endoscope, e.g., a hysteroscope, or other device, or may be used independently.

Once tissue resecting device 10 is positioned adjacent tissue to be removed, tissue resecting device 10 is activated. Activation of tissue resecting device 10 drives motor 224 which rotationally drives drive rotor 222. Rotation of drive rotor 222, in turn, drives rotation of inner cutting shaft 130 relative to elongated outer shaft 120. Activation of tissue resecting device 10 also serves to activate suction through outflow tubing 240 (in embodiments where provided), thereby applying suction through inner cutting shaft 130. With such suction applied, tissue is drawn through window 128 of elongated outer shaft 120 such that tool portion 125 facilitates cutting of tissue as a result of the rotation of blade 154a or cutting slots 160 within window 128. The suction also draws fluid and debris through inner cutting shaft 130. The tissue, fluid, and debris suctioned through inner cutting shaft 130 travel proximally through inner cutting shaft 130, inflow tubing 240, and ultimately, are deposited in a collection canister (not shown). Before, during, and/or after activation, articulation cable 127 may be displaced to articulate cutting member 150 to reposition cutting member 150 and/or blade 154a to remove additional tissue in different orientation(s). In particular, articulation of cutting member 150 may be effected while being rotated.

Tissue resecting device 10 may be utilized until the desired tissue is removed from the internal body cavity or organ. Once the desired tissue is removed, tissue resecting device 10 may be deactivated and removed from the surgical site. Thereafter, end effector assembly 100 may be disengaged from handpiece assembly 200 and discarded (or sent for reprocessing), while handpiece assembly 200 is cleaned and/or sterilized for reuse.

As an alternative to handpiece assembly 200 configured for manual grasping and manipulation during use, tissue resecting devices 10 may alternatively be configured for use with a robotic surgical system wherein the end effector assembly 100 is configured to engage a robotic arm of the robotic surgical system in a similar manner as detailed above with respect to engagement of end effector assembly 100 with handpiece assembly 200. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely control the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:
1. A tissue resecting device, comprising:
a housing including an elongated outer shaft extending from a distal end thereof, the outer shaft including a tool portion disposed at a distal end thereof, the tool portion including a window defined therein;
an inner shaft disposed within the elongated outer shaft and including proximal and distal ends, the inner shaft configured to rotate upon actuation thereof, the inner shaft including a cutting member disposed at the distal end thereof in concentric alignment with the tool portion and configured to rotate concomitantly with the inner shaft, the cutting member including:

a series of slots defined in the cutting member configured to facilitate articulation of the cutting member and cut tissue upon rotational engagement with the slots; and a blade disposed at a distal end of the cutting member configured to cut tissue upon rotational engagement therewith, the blade operably disposed within the window of the tool portion; and an actuator operably disposed on the housing and configured to articulate the tool portion and the cutting member upon actuation thereof between a neutral position wherein the blade is aligned for radial cutting and one or more articulated positions wherein the blade is aligned for varying degrees of axially-aligned cutting.

2. The tissue resecting device according to claim 1, wherein the tool portion is made from an articulatable material.

3. The tissue resecting device according to claim 1, wherein the blade is spaced from a distal end of the window of the tool portion allowing the blade to cut tissue in a more axially aligned fashion as the tool portion and cutting member are further articulated.

4. The tissue resecting device according to claim 1, wherein the tool member and the cutting member are articulatable in a range of about 0 degree and about 90 degrees.

5. The tissue resecting device according to claim 1, wherein the elongated outer shaft further includes an articulation cable coupled to a distal portion of the tool portion, such that axial displacement of the cable causes articulation of the tool portion and the cutting member between the neutral position and articulated positions.

6. The tissue resecting device according to claim 5, wherein the elongated outer shaft further includes one or more guide members configured to receive and guide the articulation cable therethrough.

7. The tissue resecting device according to claim 1, further comprising outflow tubing adapted to connect to a fluid management system configured to provide negative pressure to the outer shaft to aspirate fluids through the window and draw tissue into engagement with the blade.

8. The tissue resecting device according to claim 1, further comprising a motor disposed within the housing and configured to operably couple to the inner shaft and provide rotation thereto upon activation thereof.

9. The tissue resecting device according to claim 1, wherein the elongated outer shaft further includes an articulation cable coupled to a distal portion of the tool portion, such that axial displacement of the cable causes articulation of the tool portion and the cutting member between the neutral position and articulated positions.

10. The tissue resecting device according to claim 9, wherein the elongated outer shaft further includes one or more guide members configured to receive and guide the articulation cable therethrough.

11. A tissue resecting device, comprising:

a housing including an elongated outer shaft extending from a distal end thereof, the outer shaft including a tool portion disposed at a distal end thereof, the tool portion including a cuff at a distal end thereof and a window defined therein;

an inner shaft disposed within the elongated outer shaft and including proximal and distal ends, the inner shaft configured to rotate upon actuation thereof, the inner shaft including a cutting member disposed at the distal end thereof in concentric alignment with the tool portion and configured to rotate concomitantly with the inner shaft, the cutting member including:

a series of slots defined therein configured to facilitate articulation of the cutting member and cut tissue upon rotational engagement therewith; and a blade disposed at a distal end of the cutting member configured to cut tissue upon rotational engagement therewith, the blade selectively translatable between a blade neutral position wherein the blade is housed within the distal cuff of the tool member and a cutting position wherein the blade is aligned with the window of the tool portion; and an actuator operably disposed on the housing and configured to articulate the tool portion and the cutting member upon actuation thereof between a neutral position wherein the series of slots is aligned for radial cutting and one or more articulated positions wherein the blade, when translated to the cutting position, is aligned for varying degrees of axially-aligned cutting.

12. The tissue resecting device according to claim 11, wherein the tool portion is made from an articulatable material.

13. The tissue resecting device according to claim 11, wherein the tool member and the cutting member are articulatable in a range of about 0 degree and about 90 degrees.

14. The tissue resecting device according to claim 11, further comprising outflow tubing adapted to connect to a fluid management system configured to provide negative pressure to the outer shaft to aspirate fluids through the window and draw tissue into engagement with the series of slots or the blade.

15. The tissue resecting device according to claim 11, further comprising a motor disposed within the housing and configured to operably couple to the inner shaft and provide rotation thereto upon activation thereof.

16. The tissue resecting device according to claim 11, wherein the series of slots is laser cut, die-stamped or coined.

* * * * *